United States Patent [19]

Lee, Jr. et al.

[11] 4,340,529

[45] Jul. 20, 1982

[54] NO-MIX ORTHODONTIC ADHESIVE FORMULATIONS

[75] Inventors: Henry L. Lee, Jr., Pasadena; Giovanni Nolet, Westminster, both of Calif.

[73] Assignee: Lee Pharmaceuticals, Inc., South El Monte, Calif.

[21] Appl. No.: 139,270

[22] Filed: Apr. 11, 1980

[51] Int. Cl.³ .............................................. A61K 5/00
[52] U.S. Cl. .............................. 524/105; 260/998.11; 433/9; 433/180; 524/116; 524/854
[58] Field of Search ................... 433/217, 228, 9, 180, 433/199; 106/35; 260/998.11, 42

[56] References Cited

U.S. PATENT DOCUMENTS

| | | | |
|---|---|---|---|
| 2,916,469 | 12/1959 | Lal | 260/41 |
| 4,010,545 | 3/1977 | Kician et al. | 32/14 |
| 4,273,802 | 6/1981 | Kamada et al. | 204/159.23 |

FOREIGN PATENT DOCUMENTS 1268115 3/1972 United Kingdom .

*Primary Examiner*—Lorenzo B. Hayes
*Attorney, Agent, or Firm*—Irons and Sears

[57] ABSTRACT

In an adhesive having two curable components designed to be coated in separate layers on one or more of two surfaces to be joined, and cured upon contact of the layers with each other, one component is a curable liquid primer having a viscosity of at least 800 cps but no more than about 50,000 cps at 23° C., and the second component is a paste having a viscosity of at least 100,000 cps at 23° C. The primer is formulated with a curable liquid monomer component of which at least 30% is an alkoxy alkyl methacrylate, any balance of curable monomer in the primer comprising monomer that is capable of copolymerizing with the first-named monomer and/or cross-linking with it. Also covers the method for joining together two irregular surfaces, utilizing such an adhesive formulation. Particularly intended for orthodontic adhesive applications.

25 Claims, No Drawings

NO-MIX ORTHODONTIC ADHESIVE FORMULATIONS

RELATED APPLICATION

This application describes an improvement over the No-Mix Orthodontic Adhesive that is disclosed and claimed in U.S. pat. application Ser. No. 845,739, filed Oct. 26, 1977, now abandoned, by Jan A. Orlowski and David C. Walters. The disclosure of that application is incorporated herein by reference.

FIELD OF THE INVENTION

This invention relates to adhesive compositions generally, and specifically, to an improved orthodontic adhesive. More particularly, the invention is concerned with improved orthodontic adhesive formulations that are useful for bonding orthodontic brackets directly to tooth enamel.

BACKGROUND OF THE INVENTION

Until a few years ago, orthodontic treatment required the use of metal bands and stainless steel brackets on the teeth. In addition to being unsightly, this arrangement led to irritation of the gingiva and tongue, causing discomfort to the orthodontic patient. In addition, decalcification was often caused by the chemical reaction of band cement with tooth enamel, or by the action of microorganisms encouraged by submarginal food entrapment. These disadvantages were largely eliminated by the introduction of adhesives that had rapid set time and sufficient strength to hold the brackets in place on the teeth, eliminating the need for bands.

The development of an adhesive that is practical for securing brackets in place is difficult. The demands on such an adhesive as to physical and mechanical properties, and as to acceptability in the oral cavity, are rigorous.

Teeth are normally subjected to complex mechanical forces of shearing, grinding and impact in normal biting and chewing operations. In orthodontic treatment additional stress is imposed from the force applied by the arch-wires. A satisfactory bracket adhesive must have good resistance to shearing, grinding and impact, high tensile strength and adhesive bond strength, and must be non-brittle and resilient, so that the bracket will not break off under normal stresses in the orthodontic patient's mouth. The adhesive must also be non-toxic, non-irritating and resistant to the oral environment. A desirable adhesive should be capable of stably and retentively bonding both metal and plastic brackets to tooth surfaces for the period of the orthodontic treatment.

Adhesives heretofore used for bonding plastic or metal brackets to tooth enamel have generally been based on mono- or di-methacrylate resins and have been of two types, i.e.:

(1), a two component self-curing system consisting of a liquid and a powder, two pastes, or a paste and a liquid, which require intimate mixing prior to application to effect self-curing, or (2), a UV-cured system which cures upon exposure to light with a wavelength of 300–400 nm.

The self-curing systems have the disadvantage of limited working time. UV-cured adhesives depend upon costly and not always reliable light sources, and in addition, cannot be used with some types of brackets. In addition, the UV-curable adhesive material often does not cure properly between the confronting surface of the bracket and tooth enamel, since the adhesive layer is shielded from direct radiation.

U.S. patent application, Ser. No. 845,739, filed Oct. 26, 1977, describes an orthodontic bracket adhesive that requires no premixing and no special curing apparatus, and that can be used for bonding both metal and plastic brackets to etched tooth enamel. This adhesive consists of two components. The first component has a viscosity of between 500 cps and 750,000 cps at 23° C. and contains mono-, di-, or poly-methacrylate or acrylate ester monomers, preferably a glycidyl ester such as glycidyl methacrylate or glycidyl acrylate, or methyl methacrylate to assure proper bonding. Soluble thickening agents, fillers and cross-linking monomers may be present. Either an amine-type accelerator or a peroxide catalyst must also be present.

The second component is more viscous, preferably above 1,000,000 cps at 23° C., and contains mono-, di-, or poly-functional methacrylate or acrylate ester monomers plus a peroxide catalyst or an amine-type accelerator depending upon which the first component contains.

The viscosity of the two components is critical for the performance of the invention. The viscosity of the first component is important to assure the proper penetration of the etched tooth surface, the migration of free radicals to provide a complete and uniform cure of the adhesive, and to prevent slippage of the bracket on the tooth surface before the adhesive has cured. The second component's viscosity of above 1,000,000 cps permits the bracket to be maintained in position on the vertical tooth surface during curing of the adhesive without the need for holding it in position.

In addition, the presence of glycidyl methacrylate (GMA) has been regarded as an essential component when the adhesive is to be used with polycarbonate brackets, to provide adequate bond strength. GMA is capable of solubilizing the polycarbonate resin, which enhances the adhesive bond that is developed.

While generally the adhesive compositions described in the copending patent application have been used with great success, there is a need for other, comparable adhesive formulations, that will perform as well or better, but that utilize different monomers, so as to offer the public and the dental profession in particular greater choice.

BRIEF SUMMARY OF THE INVENTION

The present invention is based on several discoveries. It has now been found that methoxyethyl methacrylate is a monomer that is particularly useful in the formulation of two component adhesives, that, upon application to separate surfaces respectively in a sequential manner, as hereafter described, and upon juxtaposition of the coated surfaces, react to cure to bond the two surfaces together. Such formulations can be prepared to have the advantages of freedom from discoloration and decreased dermatitis potential.

It has also been found that methoxyethyl methacrylate, like GMA, solubilizes polycarbonate brackets, and thus is especially useful as a monomer ingredient in an orthodontic adhesive formulation for use with such brackets.

Adhesive formulations in accordance with the invention comprise at least two components that are formulated to be separately applicable to surfaces to be joined, and that become reactive and set when a layer of one component is placed in contact with a layer of the other component, comprising:
(a) a first component that has a sufficiently low viscosity to be flowable, readily to flow into and conform to any irregularities in a surface to which it is applied, and that comprises a liquid resin binder consisting of, in percentages by weight of the binder, at least 30% of a monofunctional ethylenically unsaturated monomer comprising methoxyethyl methacrylate, and optionally, as any balance of the monomer in the binder, a polyfunctional carboxylate selected from the group consisting of aromatic diacrylates, aromatic dimethacrylates, polyalkylene glycol diacrylates, polyalkylene glycol dimethacrylates, and mixtures thereof, and
(b) a second component that has a sufficiently high viscosity so that at least a substantial portion thereof will reside on the surface to which it is applied, and that comprises a liquid resin binder and a filler, the binder comprising from about 10% to about 70% by weight of the second component and consisting of one or more poly-ethylenically unsaturated monomers that can copolymerize with the monomer present in the component (a) binder upon curing, to form cross-linked polymer;
one of said components containing a polymerization accelerator and the other of said components containing a polymerization initiator, said accelerator and initiator being effective upon contact of layers of the two components to cause curing to occur.

DETAILED DESCRIPTION OF THE INVENTION

The adhesive compositions of the present invention are particularly designed for orthodontic applications. However they are obviously of more general use for adhering together the surfaces of a wide variety of parts, and the following description, while related to orthodontic use, is illustrative of the preferred embodiment. The same techniques are employed where other applications are intended.

The adhesive formulations of the invention have two components, referred to hereafter respectively as a primer and a paste. The primer is a liquid that is applied to both tooth and bracket base surfaces prior to application of the paste. The paste is applied thereafter. The term "paste" is used as a matter of convenience and it is intended to embrace actual pastes and, as well, thick liquids.

The primer is preferably formulated to be very thin so that it flows readily on the surface to which it is applied. For orthodontic applications, the tooth surface to which the primer is to be applied ordinarily will be etched and dried before application of the primer. The adhesive paste is highly viscous, sufficiently so that once applied to a primed tooth surface and/or a primed bracket, it will reside there or at least a substantial portion of it will, and the bracket can be pressed into the desired position and will remain there while the adhesive cures, without shifting in position.

The adhesive is a self-curing system because a curing catalyst (initiator), such as a peroxide-type catalyst, is incorporated in one component, and an accelerator is incorporated in the other component. Preferably, the accelerator is in the primer, and the catalyst is in the paste.

The viscosity of each of the two components is critical in these formulations, for good performance in orthodontic applications, although it is not critical for other less demanding applications. More is involved that the substitution of methoxyethyl methacrylate (MEM) for GMA. MEM is not as reactive a monomer as GMA, for one thing, so that the selection and concentration of comonomer(s), and of the curing system, require careful balancing to achieve desired curing times and satisfactory properties.

Also, for a general purpose orthodontic adhesive, it is necessary that good bonding be possible with all types of brackets, that is, specifically, both metal and plastic brackets. The viscosity of the liquid and paste are highly important for bonding metal (mesh) brackets, for example. If these components are too thick, mixing in situ does not occur on metal brackets, and if too thin, the mixture tends to be so fluid that the brackets float before the mixture cures.

For orthodontic applications, the viscosity of the primer should fall within the range from 800 cps to 50,000 cps at 23° C. Preferably, the viscosity of the primer is in the range from about 1,000 cps to about 5,000 cps at 23° C. The viscosity of the adhesive paste should be above 100,000 cps at 23° C., the preferred range being 100,000 cps to 300,000 cps. When the two components have viscosities in these ranges, especially in these preferred ranges, self-curing will occur readily when a layer of the paste is brought into contact with a film of the primer. Through adjustment of the relative proportions of the curing system components, curing can be caused to occur during substantially any preselected time interval. For orthodontic applications, a practical interval is from about 45 seconds to about 120 seconds, at 23° C.

If the viscosity of the primer is less than 800 cps, the mixing of the primer with the paste, which occurs when the bracket is pressed onto the tooth surface, will be insufficient to provide a complete and uniform cure. In addition, the bracket will have a tendency to slide on the tooth during the curing of the adhesive. A primer viscosity above 50,000 cps will not wet the enamel sufficiently, preventing the migration of free radicals which is necessary to produce a complete and uniform cure. If the cure is incomplete and non-uniform, the adhesive bond which is formed on curing will be very weak. Such a weak bond will not adhere well under the complex mechanical forces to which the tooth and adhesively bonded bracket will be subject—e.g., the shearing, grinding and impact involved in biting and chewing, and the stress imposed from the force applied by the arch-wires. The adhesive would then not be stable or retentive during the required treatment period.

A paste viscosity of greater than 130,000 cps permits the bracket to be maintained on the vertical tooth surface in the correct position while the adhesive is curing without the need for physically holding it in place. If the viscosity is below 130,000 cps, the bracket must be physically held in position on the tooth surface until the adhesive has cured, but the adhesive will cure properly.

The primer is made up primarily of curable ingredients, with minor quantities of other ingredients. Ordinarily the curable ingredients are a mixture of monofunctional ethylenically unsaturated monomer and difunctional ethylenically unsaturated monomer, that is, a cross-linker. The monofunctional monomer is a lower alkoxy alkyl methacrylate. In addition, other, diluent or modifying monofunctional monomer or monomers may be employed as well. The cross-linker may be selected from any one of a number of difunctional monomers.

Generally, the curable material constitutes about 75% to about 95% of the primer, but more or less may be used. A preferred amount of curable material in the primer is from about 85% to about 92%. Of the curable material, generally up to about 70% by weight may be cross-linker, which preferably is a mixture of a polyethylene glycol dimethacrylate and an ethoxylated bisphenol A dimethacrylate. However, the amount and composition of the cross-linker depend upon the properties desired in the cured product. The lower alkoxy-alkyl methacrylate may be diluted with a second monofunctional monomer if desired, but it should furnish at least 30% by weight of the curable monofunctional monomer and of the total amount of monofunctional monomer in the primer, and preferably, at least 50% or more.

The preferred curable monofunctional monomer is methoxyethyl methacrylate. It has good etching power for polycarbonate brackets. It is also a solvent for polymethyl methacrylate, so that that polymer, when used in the primer, acts as a thickener rather than as a filler. Only the monofunctional monomers have etching power for polycarbonate brackets. However, generally, the greater the etching power, the greater the propensity to act as an irritant to tissue. In this respect methoxyethyl methacrylate is very valuable, since it is a good etchant but is not an irritant. For this reason it is preferably used as the only monofunctional monomer in orthodontic adhesive formulations. The difunctional cross-linking monomers are employed to impart strength and other characteristics to primer formulations.

Several other monofunctional monomers have etching power for polycarbonates, and thus are useful either as diluents in minor amounts, or as comonomers in any proportion desired in general purpose adhesive formulations, especially those intended for use with polycarbonate plastics. Such monomers include, in order of observed decreasing ability to etch polycarbonate: methyl methacrylate, glycidyl methacrylate, methoxy ethoxy ethyl methacrylate, benzyl methacrylate, acetol methacrylate

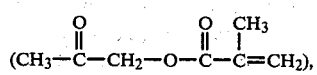

methyl glycolate methacrylate, and butyl methacrylate. Other monomers that can be used as diluents, but that have little etching power for polycarbonates, include phenyl methacrylate, trichloroethane methacrylate, 1,3-dichloro-2-propyl methacrylate, p-cresyl methacrylate, crotyl methacrylate, and tetrahydrofurfuryl methacrylate.

Among the cross-linking monomers herein contemplated are 2,2 bis [4'(-3"-methacryloyl-2"-hydroxypropoxy)phenyl] propane (known as Bis/GMA); mono-, di-, tri- tetra-, and polyethylene glycol dimethacrylates; diallyl succinate; 2,2-bis [4'(2") methacryloyl ethoxy phenyl] propane; diallyl phthalate; bis (2-methacryloylethyl) o-, m-, and p-phthalates; and 2-acryloylethylmethacrylate. Another preferred cross-linking monomer is a mixture of Bis/GMA and diethylene glycol dimethacrylate. The proportions generally are selected to produce a desired viscosity, which, for the entire paste, is of course directly affected by the kind and amount of filler and/or thickener employed.

Other similar cross-linking monomers having at least two groups or moieties, such as allyl, acryloyl, methacryloyl and other similar unsaturations, capable of polymerizing in the presence of the initiators and accelerators of the present invention are contemplated. Typically, these monomers are not only mono-polymerizable, so to speak, and co-polymerizable, but they are suitable crosslinking agents for acrylic polymers. Monomers of low viscosity ordinarily are selected, except for use in small amounts.

The minor components that ordinarily are incorporated in the primer include such materials as the accelerator, which is ordinarily a tertiary amine accelerator, a stabilizer, an ultraviolet light absorber or stabilizer, and generally, a polymeric filler material.

The accelerators within the purview of the instant discovery and preferred are the tertiary amines, especially N,N-di(lower) alkyl-p-toluidines (e.g., N,N-dimethyl-p-toluidine, N,N-diethyl-p-toluidine) and N,N-di (lower) alkyl anilines, such as N,N-dimethyl aniline.

The polymeric filler may be soluble, partially soluble, or insoluble in the primer. Suitable polymeric fillers are the polymers and copolymers of methyl and ethyl methacrylate; the polymers and copolymers of methyl, ethyl, and propyl acrylate; and generally, polymers of the monoacrylates and monomethacrylates, particularly the lower alkyl esters. Because of the need for flowability, the amount of filler in the primer is necessarily at a very low level, generally from zero to about 25%. More than 25% may be used if desired, provided the viscosity of the primer component is below 50,000 cps at 23° C.

The preferred stabilizer is 3-butyl-4-hydroxytoluene. Other modifiers may also be present in minor conventional amounts, such as, for example, dyes, opaquing agents, and other special purpose modifiers.

The paste component generally is formulated with a liquid resin compound that contains from about 10% to about 60%, and preferably 20% to 50%, by weight of the liquid resin of monomers selected from the group consisting of mono-, di-, and poly- alkylene glycol diacrylate or dimethacrylate esters and mixtures thereof. These monomers not only are useful cross-linkers per se but also act as diluents that are useful in adjusting paste viscosity to lower levels. Often a mixture will be employed to facilitate adjustment of the viscosity to a desired level. The remainder of the liquid resin component is generally formulated from one or more aromatic dimethacrylates of high viscosity, such as, for example, 2,2-bis [4'-(3" methacryloyl-2"-hydroxy propoxy) phenyl] propane (known as Bis/GMA), or the like.

The paste component also will contain a total amount in the range from about 30% to about 90%, preferably from 45% to 60%, by weight of the paste of "filler". The term "filler" is used to include thickening agent material, which may be soluble or partially soluble, and more conventional filler materials, which may be organic or inorganic. The paste also contains the catalyst, preferably, which may be impregnated in a filler material. The thickening agent and the filler materials, like all of the materials employed, must be physiologically acceptable and insoluble in the fluids encountered in the oral cavity. Exemplary materials include silica, cellulose acetate butyrate, and finely divided polymeric material such as polymethylmethacrylate, polyethylmethacrylate, and copolymeric methyl/ethyl methacrylate. Whether the filler is organic or inorganic, it is preferably utilized in finely divided form with a particle size in the range from about 1 micrometer to about 30 micrometers.

The paste may also contain other conventional modifiers in minor amounts, such as, for example, dyes, opaquing agents such as titanium dioxide, stabilizers, and inhibitors of the hydroquinone or hydroxytoluene type.

The curing system for the two component adhesive system is made up of the catalyst (initiator) and the accelerator, generally a peroxide catalyst and a tertiary amine accelerator. These are kept separate from each other, to make the separate components storage stable, as is well known in the art. Generally it is advantageous to incorporate the peroxide catalyst in the paste together with inorganic filler material, while the accelerator is a part of the primer. If the primer and the paste were to be mixed together, the respective amounts of catalyst and of accelerator would be in ranges that are well recognized in this art. That is, the amount of catalyst such as benzoyl peroxide would be in the range from about 0.2% to about 8%, and the amount of the accelerator, such as N,N-dimethyl-p-toluidine, would be in the range from about 0.1% to about 8%, these percentages being by weight based on the total weight of the adhesive composition.

The invention will be more easily understood by reference to the following specific examples, which describe several demonstrations of the invention. All parts and percentages in these examples and elsewhere in the specification are by weight unless expressly stated to be otherwise. Similarly, temperatures are in degrees Celsius unless otherwise specified. Viscosity measurements are based on observations made employing a Brookfield viscometer, Model RBT, Spindle No. 5, operated at 20 rpm, at 23° C.

EXAMPLES

Orthodontic Adhesive Formulations

The following are representative primer formulations.

TABLE 1

| | Primer Formulations | | | | |
|---|---|---|---|---|---|
| | Primer Parts by Weight | | | | |
| Ingredient | 1 | 2 | 3 | 4 | 5 |
| methoxyethyl methacrylate | 5 | 5 | 5 | 5 | 15 |
| diethylene glycol dimethyacrylate | 5 | 2 | 2 | 2 | 6 |
| ethoxylated bis-phenol A dimethacrylate | — | 3 | 3 | 3 | 9 |
| t-butyl hydroxy toluene | 0.006 | 0.006 | 0.006 | 0.006 | 0.018 |
| Spectrasorb, U.V. inhibitor (2 hydroxy methoxy benzophenone) | 0.05 | 0.05 | 0.05 | 0.05 | 0.15 |
| polymethyl methacrylate powder | 1.6 | 1.0 | 1.0 | 1.0 | 3.3 |
| N,N-bis (2-hydroxyethyl)-p-toluidine | 0.2 | 0.2 | 0.1 | 0.46 | 1.41 |

Because of their high contents of accelerator, Primers 4 and 5 are very fast setting. Primer 2 is preferred for general orthodontic use, as to setting rate.

Representative paste formulations are as follows:

TABLE 2

| | Paste Formulations | | | | |
|---|---|---|---|---|---|
| | Paste Formulations by Weight | | | | |
| Ingredient | 1 | 2 | 3 | 4 | 5 |
| 2,2-bis[4'-3''-methacryloyl-2''-hydroxypropoxy) phenyl] propane | 60.0 | 60.0 | 79.6 | 75 | 105 |
| 2,2-bis[4'(2'' methacryloxyl ethoxy) phenyl] propane | 20.0 | — | — | — | — |
| triethylene glycol dimethacrylate | 20.0 | 40.0 | — | — | — |
| diethylene glycol dimethacrylate | — | — | 26.5 | 25 | 45 |
| amorphous silica | 200.0 | 150.0 | 52.8 | 55 | 57.6 |
| cellulose acetate butyrate | 60.0 | — | — | — | — |
| titanium dioxide | — | — | 0.1 | — | 0.15 |
| benzoyl peroxide (BPO) | 3.0 | 3.0 | 5.5 | 6.0 | 14.4 |
| hydroquinone | 0.1 | — | — | — | — |
| Spectrasorb U.V. inhibitor | — | — | 0.5 | — | 0.75 |
| t-butyl hydroxy toluene | — | 0.2 | 0.06 | 0.06 | 0.09 |

In preparing the paste, the silica and BPO may be mixed separately, preferably with a small amount of an organic solvent such as $CH_2Cl_2$ sufficient to wet the silica particles. This premix of filler is then blended with the other ingredients of the paste.

An adhesive composition can be made by combining any one of the primer formulations with any one of the paste formulations. The preferred technique for combining a primer and paste is by applying primer to the surfaces to be joined, then applying paste to one or both of these primer surfaces, then joining them, applying pressure as needed until the adhesive has set. These formulations have been prepared to permit approximately 1:1 usage. However, the proportions used of each may be varied, within reasonable limits of say 3:1 to 1:3, while achieving acceptable results.

Primers 2 through 5 above represent preferred formulations.

The primer and paste compositions indicated in Table 1 below were evaluated by using them to adhere a plastic orthodontic bracket to an etched, dried, bovine tooth surface, The set time for each composition was observed, and in addition, the adhesion value at failure was observed in each case after storage for one day in a water bath at 37° C. Each value reported is an average of several observations on several samples.

TABLE 3

| | Adhesive Compositions | | |
|---|---|---|---|
| Primer | Paste | Setting time, Seconds (at) | Adhesion in lbs. |
| 1 | 3 | 30 (23.8° C.) | 10.9 |
| 2 | 3 | 39 (22° C.) | 14.5 |
| 2 | 3 (replication) | | 16.7 |
| 2 | 3 (replication) | 39 (22.4° C.) | 21.9 |
| 3 | 3 | 39.3 (22.4° C.) | — |
| 4 | 3 | 10–11 secs. (26° C.) | 16.8 |
| 4 | 3 (replication) | 10–11 secs. (26° C.) | 23.2 |
| 4 | 3 (replication) | 16.7 (22.4° C.) | 22.2 |
| 5 | 3 | | 11.6* |
| 5 | 3 | | 12.9** |
| 5 | 5 | 47 (24.6° C.) | 22.3*** |

TABLE 3-continued

| | Adhesive Compositions | | |
|---|---|---|---|
| Primer | Paste | Setting time, Seconds (at) | Adhesion in lbs. |
| 5 | 5 | — | 19.1** |

*Metal bracket; after storage in water bath for 3 days at 37° C.
**After storage in water bath for 3 days at 37° C.
***After storage in water bath for 1 day at 37° C.

Other evaluations were carried out using Primer-2 and Paste-3. After storage of samples for one week in a water bath at 37° C., adhesion at break was 17.6 lbs. After two weeks in the bath, adhesion at break was about 21 lbs. The primer was stored for two weeks at room temperature, then evaluated. Set time at 22° C. remained 39 seconds, and adhesion value at failure was close to 16 lbs. (these values, like other test results reported herein, are averages taken from observations on several specimens). After storage of the primer at 37° C. for two weeks, setting time at 22° C. remained 39 seconds, and the adhesion value was about 19 lbs. After storage of the primer in a refrigerator for two weeks, setting time at 22° C. remained 39 seconds, and adhesion at break was about 18 lbs.

Samples of Primer-2 were subjected, respectively, to storage for three weeks at room temperature, three weeks at 37° C., and three weeks in the refrigerator. All samples remained stable. These samples, after storage, were then mixed with Paste 3 and evaluated in an orthodontic environment, adhering plastic brackets to bovine tooth enamel. For those samples where the liquid had been stored for three weeks at 37° C., the adhesion value at failure was 18.9 lbs. The samples from liquid (primer) stored at room temperature produced an adhesion value of about 14 lbs., while for those from primer stored in the refrigerator, the value was about 20 lbs. In the case where the primer had been stored for 1 day in a water bath, for comparison, the adhesion at break was about 18 lbs.

Primer-3 is very similar to Primer-2, except that the amount of accelerator has been reduced by ½. This increases the setting time and permits the orthodontist longer working time as desired. It also facilitates evaluations, where mechanical testing is involved.

Other evaluations were made on the adhesive prepared from the use of Primer-3 with Paste-3, with the following observed results:

TABLE 4

| Properties, Adhesive from Primer-3 and Paste-3 | |
|---|---|
| Rockwell Hardness (after 1 day in a water bath) | 118 |
| Staining | good resistance |
| Discoloration | good resistance |
| Diametral tensile strength | approx. 3,530 psi |
| Diametral tensile strength after submersion in a water bath for 1 week | 4,090 psi |
| after 2 weeks | 3,665 psi |
| after 4 weeks | 3,419 psi |
| Set time at 22° C. | 29 seconds |

When this combination was used to adhere plastic orthodontic brackets to etched, dried bovine tooth surfaces, set times was about 39 seconds at 22° C. After one day in a water bath, the average adhesion value at break was 21.9 lbs; after 2 weeks in the water bath, 15.6 lbs; after 2 weeks in a water bath at 37° C., 21.2 lbs.

Other evaluations were made on the adhesive prepared by using Primer-3 and Paste-3 together, with the following observed results.

After the sample had been submerged four weeks in a water bath at room temperature the adhesion value at break was observed to be about 18.7 lbs. In a related evaluation, after the primer had been stored for four weeks at room temperature and then tested, the adhesion value at break was about 20 lbs.

Primer-3 remains stable after storage for four weeks at room temperature, for four weeks at 37° C., and for four weeks in the refrigerator. When the primer samples that had been stored for four weeks at 37° C. were evaluated in an orthodontic type evaluation for securing a plastic bracket to a bovine tooth surface, the adhesion value at break was about 16.2 lbs. Similarly, with the primer that had been stored for four weeks in the refrigerator, the adhesion value at break was about 20 lbs; after 5 weeks at room temperature, about 18.5 lbs; 5 weeks at 37° C., 19.9 lbs; 5 weeks in the refrigerator, about 20.7 lbs.

Adhesion values at failure were compared for metal brackets and for plastic brackets in a separate series of observations, made after storage in a water bath (metal, 1 day storage; plastic, 2 months storage), as reported in Table 2 below.

TABLE 5

| Adhesion Properties of the Primer-3 and Paste-3 Combination | | | |
|---|---|---|---|
| Primer | Paste | Bracket | Adhesion in Lbs. |
| 3 | 3 | plastic | 18.1 |
| 3 | 3 | metal | 12.1 |

The length of storage affects the adhesion value; in another test with metal brackets, after 1 week in a water bath, the adhesion at break was about 15 lbs. Water sorption is about 1.2 mg/cm$^2$ after 1 week's immersion.

Similar evaluations conducted after even longer storage periods did not show substantial deterioration in properties. Comparable results are obtained when each primer formulation above is utilized with each paste. All form good general purpose adhesives. All are useful as orthodontic adhesives, with plastic brackets. Generally the use of a cross-linker in the formulation is preferred, for structural strength.

Orthodontic Adhesive Formulations; Second Series

A series of primers of different compositions was made up and evaluated, to demonstrate the effects and importance of changes in ingredients and in their respective proportions. The several compositions are reported below in Table 3.

TABLE 6

| Ingredient | 2-1 | 2-2 | 2-3 | 2-4 | 2-5 | 2-6 | 2-7 | 2-8 | 2-9 | 2-10 | 2-11 | 2-12 | 2-13 | 2-14 | 2-15 | 2-16 | 2-17 | 2-18 |
|---|---|---|---|---|---|---|---|---|---|---|---|---|---|---|---|---|---|---|
| methoxyethyl methacrylate diethylene | 3 | 4 | 2 | 5 | 6 | 7 | 2 | 2 | 1 | 1 | 5 | 3 | 7.5 | — | 5 | 10 | — | — |

TABLE 6-continued

| Ingredient | 2-1 | 2-2 | 2-3 | 2-4 | 2-5 | 2-6 | 2-7 | 2-8 | 2-9 | 2-10 | 2-11 | 2-12 | 2-13 | 2-14 | 2-15 | 2-16 | 2-17 | 2-18 |
|---|---|---|---|---|---|---|---|---|---|---|---|---|---|---|---|---|---|---|
| glycol methacrylate | 4 | 2 | 3 | 1 | 2 | 1 | 2 | 6 | 4.5 | 2 | 4 | 1 | 1.5 | 5 | — | — | 10 | — |
| ethyloxylated bisphenol A dimethacrylate | 3 | 4 | 5 | 4 | 2 | 2 | 6 | 2 | 4.5 | 7 | 1 | 6 | 1.0 | 5 | 5 | — | — | 10 |
| t-butyl hydroxy toluene | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 | 0.006 |
| 2-hydroxy methoxy benzophenone | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 |
| polymethyl methacrylate powder | 0.8 | 0.6 | 0.06 | 0.72 | 0.83 | 0.95 | 0.7 | 0.95 | 0.7 | 0.6 | 1.5 | 0.7 | 1.5 | 0.65 | 0.65 | 0.8 | 0.8 | — |
| N,N-bis (2 hydroxyethyl) p-toluidine | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 | 0.18 |

For evaluation purposes, the several primers described above were evaluated by using each, with Paste-3, to adhere a plastic orthodontic bracket to an etched, dried, bovine tooth surface. The adhesion value at failure was observed in each case after storage for one day in a water bath at 37° C. As before, each value reported is an approximate average of several observations on several samples.

TABLE 7

Adhesion Properties for Several Compositions

| Primer | Adhesion in lbs. |
|---|---|
| 2-1 | 9.8 |
| 2-2 | 19 |
| 2-3 | 5.5 |
| 2-4 | 9.0 |
| 2-5 | 9.0 |
| 2-6 | 16.7 |
| 2-7 | * |
| 2-8 | 6.7 |
| 2-9 | 3.5 |
| 2-10 | * |
| 2-11 | 19.1 |
| 2-12 | * |
| 2-13 | 17.5 |
| 2-14 | * |
| 2-15 | |
| 2-16 | 15.6 |
| 2-17 | 12.2 |
| 2-18 | * |

*Very weak adhesion; brackets released from teeth readily.

The brackets adhered with adhesives prepared from Primers 2-7, 2-10, 2-12, 12-14 and 2-18 exhibited very weak adhesion. Each of these primers contains a very small proportion, or none at all, of the monomer, methoxyethyl methacrylate. All of these adhesives featured a very fast set time, so that the primer has very little time to etch the surfaces of the plastic brackets.

The adhesive prepared from Primer 2-16 was acceptable for use with plastic brackets although its properties were not optimum. Since it was not acceptable for use with metal brackets, adhesives prepared from primers containing a cross-linker would ordinarily be preferred for commercial purposes, since the flexibility to work with any kind of bracket would be desired.

Preferred primer formulations for orthodontic adhesive applications are those within the following approximate ranges of composition, expressed in percentages by weight of the liquid resin binder:

| | |
|---|---|
| methoxyethyl methacrylate | 30-70 |
| diethylene glycol dimethacrylate | 5-45 |
| ethoxylated bisphenol A dimethacrylate | 10-40 |

General

While the invention is particularly concerned with improved orthodontic adhesive formulations, it is not so limited. The primer-paste combinations disclosed in accordance with the present invention can be used for adhering together many different articles, such as, for example, plastic to plastic, metal to plastic, metal or plastic to tooth enamel, and the like. Best results are observed when the surfaces to be joined are irregular.

For orthodontic applications, it is preferred that the amount of catalyst and initiator in the system be adjusted to produce an overall setting time of about 45 to 50 seconds at room temperature. However, setting time is sensitive to temperature, and high room temperatures can speed up the setting time whereas the use of a refrigerated product can slow down the setting time.

To use primer-paste materials formulated in accordance with the present invention, for orthodontic applications, the following procedure can be followed. First, the primer is brushed onto each etched, dry tooth, over the area to which the bracket is to be bonded. The primer is then applied to the underside of each bracket base or pad. It is applied as a thin, uniform coating. A small quantity of adhesive paste is then placed on each primed bracket base, using as little material as is needed to provide complete coverage of the base. If a rapid setting formulation is being employed, it may be necessary to apply the adhesive paste to a single bracket at any one time. Each bracket is then placed on the tooth and pressed lightly in the desired position. The bracket position may be adjusted for a few seconds, before setting occurs, by sliding it gently over the primed tooth surface. When the proper position has been obtained, the bracket should be pressed firmly against the tooth. The bracket is then permitted to remain in place without stress of any kind until setting has been completed.

Excessive adhesive can then be removed. After about five minutes, the arch wire can be applied and tied down. Ordinarily, the adhesive should be formulated to achieve about 50% of its full strength in the first sixty seconds while it is setting, and about 90% of its full strength in the following four minutes.

A generally similar procedure is used for securing together any other articles desired. The etching step used for orthodontic work provides an irregular surface which the primer can wet and penetrate. For other applications, a similar roughing technique may or may not be advisable, depending upon the nature of the surfaces to be joined.

The term monofunctional is used herein to refer to a monoethylenically unsaturated monomer such as an acrylate or methacrylate that has no other functional group as used.

For general purpose adhesive formulations, up to 70% of the monofunctional curable monomer in the primer may be a diluent monomer, preferably selected from among those named above or from the family of alkoxyalkyl methacrylates, preferably lower alkoxy, lower alkyl methacrylates or closely related compounds such as, for example, methoxy ethoxy ethyl methacrylate. The remainder should be methoxyethyl methacrylate.

Conclusion

While the invention has been disclosed herein by reference to the details of preferred embodiments thereof, it is to be understood that such disclosure is intended in an illustrative rather than in a limiting sense, and it is contemplated that various modifications in the compositions of the invention will readily occur to those skilled in the art, within the spirit of the invention and the scope of the appended claims.

What is claimed is:

1. An orthodontic adhesive composition that becomes reactive and set when a layer of one component is placed in contact with a layer of the other component, comprising:
    (a) a first component having a viscosity in the range of about 800 cps to about 50,000 cps at 23° C. comprising a liquid resin binder consisting of, in percentages by weight of the binder, at least 30% of a monofunctional ethylenically unsaturated monomer comprising methoxyethyl methacrylate, and optionally, as additional monomer in the binder, a polyfunctional carboxylate selected from the group consisting of aromatic diacrylates, aromatic dimethacrylates, polyalkylene glycol diacrylates, polyalkylene glycol dimethacrylates, and mixtures thereof, and
    (b) a second component having a viscosity greater than about 100,000 cps at 23° C. comprising a liquid resin binder and a filler, the binder comprising from about 10% to about 70% by weight of the second component and consisting of one or more polyethylenically unsaturated monomers that can copolymerize with the monomer present in the component (a) binder upon curing, to form cross-linked polymer;
one of said components containing an effective amount of a polymerization accelerator and the other of said components containing an effective amount of a polymerization initiator, said accelerator and initiator being effective upon contact of layers of the two components that have been separably applied to cause curing to occur.

2. The orthodontic composition of claim 1 wherein the resin binder of the first component comprises 30% to 70% by weight of the binder of methoxyethyl methacrylate.

3. The orthodontic composition of claim 2 wherein the binder of the first component consists of a mixture of the methoxyethyl methacrylate with from 5% to 45% of a poly(ethylene glycol) dimethacrylate and from 10% to 40% of an ethoxylated bisphenol A dimethacrylate, the percentages being by weight of the binder.

4. The orthodontic composition of claim 1, 2 or 3 wherein the binder of the second component is a mixture of an aromatic dimethacrylate with a poly (alkylene glycol) dimethacrylate.

5. The orthodontic composition of claim 4 wherein the binder of the second component is a mixture of a poly(ethylene glycol) dimethacrylate and the dimethacrylate of the diglycidyl ether of bisphenol A.

6. An adhesive comprising two curable components designed to be coated in separate layers on one or more of two surfaces to be joined, and cured upon contact of the layers with each other, comprising:
    (a) a primer component comprising curable liquid resin binder, said primer having a viscosity of at least 800 cps but no more than 50,000 cps at 23° C., said binder comprising curable monomer, at least 30% of the curable monomer in the primer consisting of a lower alkoxy-alkyl methacrylate, any balance of curable monomer in the primer comprising monomer that is capable of copolymerizing with said first-named monomer and/or cross-linking with it upon curing; and
    (b) a paste component comprising in admixture a curable liquid monomer and filler, said paste having a viscosity of at least 100,000 cps at 23° C.;
one of said components containing a polymerization accelerator and the other of said components containing a polymerization initiator, said accelerator and initiator being effective upon contact of the layers of the two components to cause curing to occur.

7. The orthodontic adhesive of claim 6 wherein said lower alkoxyalkyl methacrylate is methoxy ethyl methacrylate.

8. The orthodontic adhesive of claim 7 wherein from about 30% to about 70% of the curable monomer in the primer is the methoxyethyl methacrylate.

9. The orthodontic adhesive of claim 8 wherein the adhesive composition is dermatologically acceptable.

10. The orthodontic adhesive of claim 8 wherein the balance of curable monomer in the primer comprises a mixture of a polyethylene glycol dimethacrylate with an ethoxylated bisphenol A dimethacrylate.

11. The orthodontic adhesive of claim 6, 7 or 8 wherein the liquid monomer in the paste component consists essentially of monomer that is capable of copolymerizing with and cross-linking with the monomer of the primer.

12. The orthodontic adhesive of claim 11 wherein the liquid monomer in the paste component comprises an aromatic dimethacrylate.

13. The orthodontic adhesive of claim 12 wherein the liquid monomer of the paste component also comprises a polyethylene glycol dimethacrylate.

14. The orthodontic adhesive of claim 6, 7 or 8 wherein the primer comprises from 5% to 25% by weight thereof of a filler material selected from the group consisting of organic filler material, inorganic filler material, and mixtures thereof.

15. The orthodontic adhesive of claim 6, 7 or 8 wherein the paste component consists of 10% to 70% by weight of a curable liquid resin binder consisting of monomer selected from the group consisting of aromatic dimethacrylates and diacrylates, polyethylene glycol dimethacrylates and diacrylates, and mixtures thereof, 30% to 90% by weight of organic or inorganic filler material or mixtures thereof, and about 1% to about 10% by weight of a curing agent comprising a polymerization accelerator or initiator selected from the group consisting of a tertiary aromatic amine and an organic peroxide.

16. The orthodontic adhesive of claim 15 wherein the balance of curable monomer in the primer is a mixture of a polyethylene glycol dimethacrylate and an ethoxylated bisphenol A dimethacrylate, and wherein the curable liquid monomer of the paste is a mixture of a major amount of 2,2-bis[4'-(3" methacryloyl-2" hydroxypropoxy) phenyl] propane and a minor amount of a polyethylene glycol dimethacrylate.

17. The orthodontic adhesive of claim 16 wherein the primer contains an effective amount of a tertiary amine accelerator and the paste contains an effective amount of an organic peroxide catalyst, for causing curing in up to about 120 seconds, upon contact of a layer of the primer with a layer of the paste.

18. An orthodontic adhesive suitable for bonding a metal or plastic bracket to tooth enamel which comprises two curable components designed to be coated in separate layers on one or more of two surfaces to be joined and cured upon contact of the layers with each other, said components comprising:
(a) a primer component consisting of from 5% to about 25% by weight thereof of filler material and at least about 75% by weight thereof of curable liquid monomer, at least 30% of said curable monomer being methoxyethyl methacrylate, and any balance comprising monomer selected from the group consisting of mono-, di-, and poly- methacrylate or acrylate ester monomers and mixtures thereof, and an amount up to 10% by weight of one or the other of a polymerization accelerator or initiator catalyst selected from the group consisting of a tertiary aromatic amine and an organic peroxide, respectively, the primer component having a viscosity of at least 800 cps but no more than 50,000 cps at 23° C., and
(b) a paste component comprising from about 20% to about 80% by weight thereof of curable liquid monomer selected from the group consisting of mono-, di-, and poly- methacrylate or acrylate ester monomers and mixtures thereof, from about 30% to about 90% by weight of organic or inorganic filler or a mixture thereof, and up to 10% by weight of the one not in the primer of a polymerization accelerator or initiator selected from the group consisting of a tertiary aromatic amine and an organic peroxide, respectively, the paste component having a viscosity of at least 100,000 cps at 23° C.

19. The orthodontic adhesive of claim 18 wherein the primer component contains 8% to 15% by weight thereof of filler.

20. The orthodontic adhesive of claim 18 wherein the curable binder of the primer comprises from about 30% to about 70% by weight thereof of the methoxyethyl methacrylate, the balance comprising a mixture of aliphatic and aromatic dimethacrylates.

21. The orthodontic adhesive of claim 20 wherein the balance of the curable binder in the primer is a mixture of a polyethylene glycol dimethacrylate and an ethoxylated bisphenol A dimethacrylate.

22. The orthodontic adhesive of claim 18, 20 or 21, wherein the curable liquid binder constitutes from 85% to 92% by weight of the primer.

23. The orthodontic adhesive of claim 20 or 21 wherein the liquid monomer in the paste component comprises from about 10% to about 60% by weight of the liquid monomer of a mono-, di-, or poly-alkylene glycol dimethacrylate, the balance being aromatic dimethacrylate.

24. The orthodontic adhesive of claim 22 wherein the liquid monomer in the paste component comprises from about 10% to about 60% by weight of the liquid monomer of a mono-, di-, or poly- alkylene glycol dimethacrylate, the balance being aromatic dimethacrylate.

25. An orthodontic adhesive that is suitable for bonding a metal or plastic bracket to the surface of a tooth, said adhesive comprising two curable components designed to be coated in separate layers on one or more of the bracket and tooth surfaces that are to be secured together respectively, the two curable components being curable upon contact of the layers with each other, since components comprising:
(a) a primer component consisting essentially of from about 8% to about 15% of the primer component of a filler, and from about 85% to about 92% by weight of the primer component of a liquid resin binder, said binder consisting of a mixture of from 30% to 70% by weight of the binder of methoxyethyl methacrylate, from 5% to 45% by weight of the binder of diethylene glycol dimethacrylate, and from 10% to 40% by weight of the binder of ethyloxylated bisphenol A dimethacrylate, said primer component having a viscosity in the range from 1,000 to 5,000 cps at 23° C., and
(b) a paste component consisting essentially of from 30% to 90% by weight thereof of filler material, the balance being a curable liquid resin binder, said binder comprising from 20% to 50% by weight of the binder of monomers selected from the group consisting of mono-, di-, and poly- alkylene glycol dimethacrylates and mixtures thereof, the balance of the liquid resin binder being an aromatic dimethylacrylate of high viscosity, the paste component having a viscosity in the range from about 130,000 to about 300,000 cps at 23° C.;
one of said components containing a polymerization accelerator and the other of said components containing a polymerization initiator, said accelerator and initiator being effective upon contact of the layers of the two components to cause curing to occur.

* * * * *